United States Patent [19]
Hoover

[11] Patent Number: 5,159,921
[45] Date of Patent: Nov. 3, 1992

[54] SURGICAL RETRACTOR

[76] Inventor: Rocklin L. Hoover, Rte. 3, Box 314-X, Sumter, S.C. 29154

[21] Appl. No.: 618,393

[22] Filed: Nov. 27, 1990

[51] Int. Cl.$^5$ .............................................. A61B 17/02
[52] U.S. Cl. ..................................................... 128/20
[58] Field of Search ..................... 128/20, 87 R, 89 R; 606/192, 193, 196

[56] References Cited

U.S. PATENT DOCUMENTS

| | | | |
|---|---|---|---|
| 3,522,800 | 8/1940 | Lesser | 128/20 |
| 3,592,198 | 7/1971 | Evans | 128/352 |
| 3,745,998 | 7/1973 | Rose | 128/89 R |
| 3,762,404 | 10/1973 | Sakita | 128/78 |
| 3,782,370 | 1/1974 | McDonald | 128/20 |
| 3,796,214 | 3/1974 | Davis | 128/6 X |
| 3,807,393 | 4/1974 | McDonald | 128/20 |
| 3,863,639 | 2/1975 | Kleaveland | 128/303 |
| 4,562,832 | 1/1986 | Wilder et al. | 128/20 |
| 4,597,030 | 6/1986 | Brody et al. | 128/20 X |
| 4,657,003 | 4/1987 | Wirtz | 128/89 R X |
| 4,719,918 | 1/1988 | Bonomo et al. | 606/192 |
| 4,848,364 | 7/1989 | Bosman | 128/87 R X |
| 4,885,811 | 12/1989 | Hayes | 128/89 R X |
| 4,984,564 | 1/1991 | Yuen | 128/20 |

FOREIGN PATENT DOCUMENTS

| | | | |
|---|---|---|---|
| 0797668 | 1/1981 | U.S.S.R. | 128/20 |
| 1246994 | 7/1986 | U.S.S.R. | 128/20 |
| 1367948 | 1/1988 | U.S.S.R. | 128/20 |

*Primary Examiner*—John G. Weiss
*Assistant Examiner*—Nicholas D. Lucchesi
*Attorney, Agent, or Firm*—Michael A. Mann

[57] ABSTRACT

A surgical retractor for holding an incision in an open configuration comprising a compartment that has a flexible condition for placing the compartment into engagement with the tissue of the incision and a rigid condition for holding the tissue apart. The compartment contains elastically compressible beads and a fluid such as air and changes to the rigid condition by evacuating the air through the valve so that the wall of the compartment collapses to pack the beads together in a monolith of the desired shape. The compartment, which may be in the shape of an oval or an elongated tube, has a thickened portion oriented interior to the incision for preventing punctures, which carries optionally a light source such as a fiber optic bundle for illuminating the surgical area and also a suction source for evacuation of fluids, vapors, odors or smoke from the operative site.

13 Claims, 2 Drawing Sheets

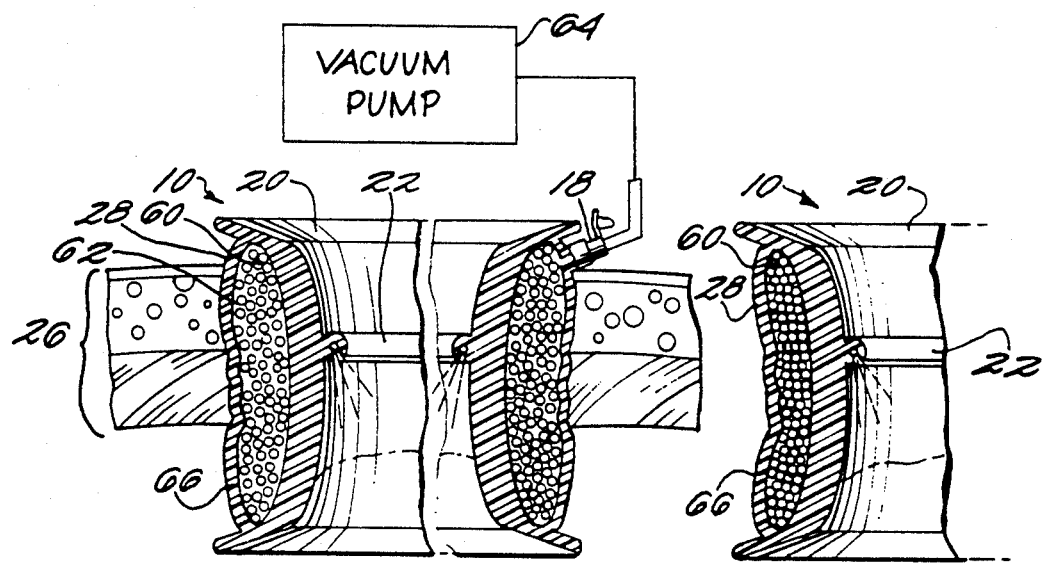
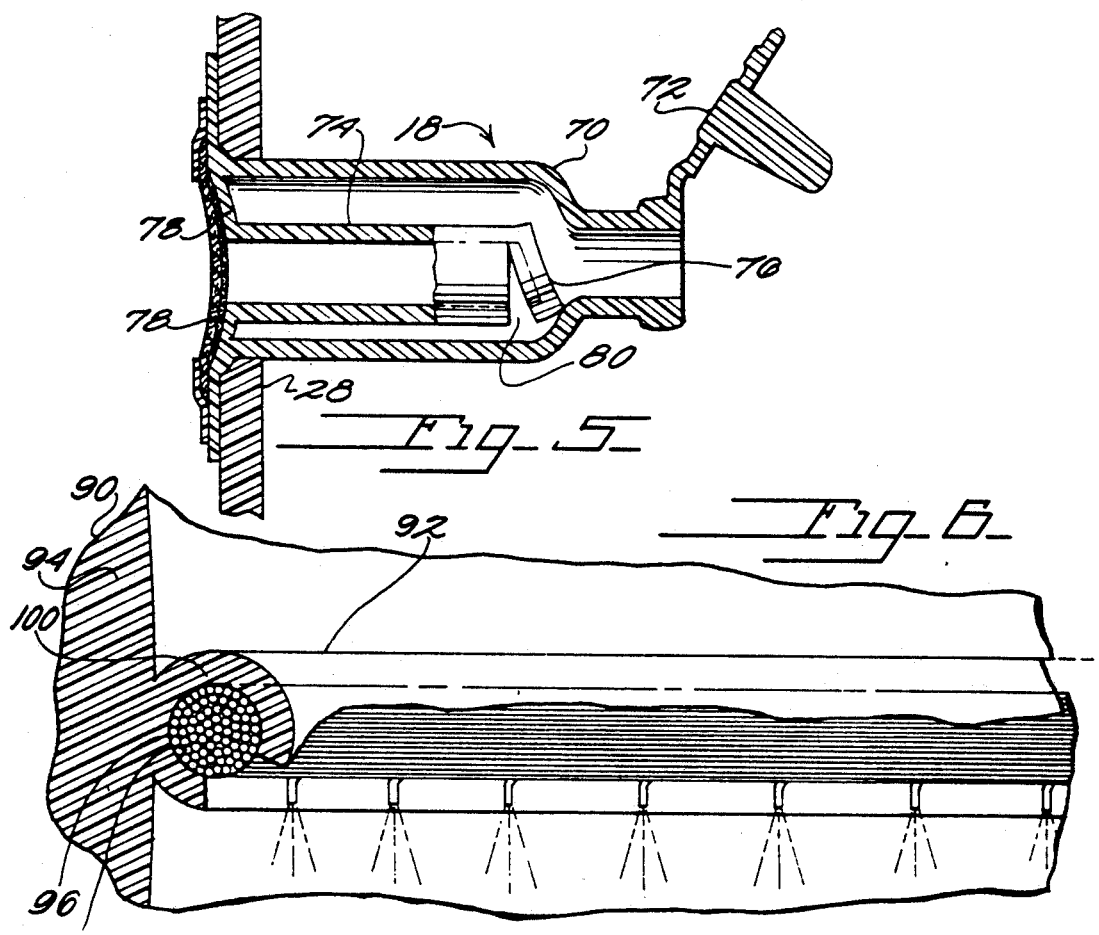

SURGICAL RETRACTOR

BACKGROUND OF THE INVENTION

1. Field of the Invention

This invention relates to surgical devices, more particularly retractors for holding an incision or natural body orifices in an open position during surgery.

2. Discussion of Background

In the past, a variety of retractors have been employed in surgical procedures for spreading apart the sides of an incision or the natural body orifices. Typically these retractors are made of steel so as to be sterilizable for surgical procedures. These instruments are quite heavy and stout in order to supply the substantial forces needed to open and keep open an operative site. Hand retractors typically have a broad hook-like flap at oneend for fitting over the tissue to be retracted then pulled apart by hand and held or clamped during the surgical procedure. Another surgical retractor has a rigid peripheral ring with several detachable and movable blades which can be clamped at any point on the ring to hold open the surgical site. Still another type retractor has arms that are interconnected by a gear or rack and pinion arrangement so that they can be cranked apart and locked into position. These instruments have numerous parts, are costly and require complicated assembly and disassembly for use and sterilization. An additional problem associated with these retractors is they cause trauma to the tissue retracted by the relatively large force exerted on a relatively small area of tissue.

Another problem in surgical procedures is providing uninterrupted lighting to the operative site. Illumination sources include overhead lighting, portable multidirectional lighting worn by the surgeon or mounted to a clamp placed near the incision, or other sources supplied from outside the incision. The light which is supplied to the operative site is often blocked by the surgeons' arms and other objects between the light source and the operative site.

There is a need for a retractor that is easy to put into place and maintain while minimizing trauma to the retracted tissue and supplying illumination to the operative site. Such a retractor should be capable of distributing the necessary force to spread the tissues over a much wider area of tissue, and be made of durable, sterilizable material.

SUMMARY OF THE INVENTION

In accordance with its major aspects, the present invention is a retractor for maintaining an incision or natural body orifices in an open position and providing, in a preferred embodiment, a source of light interior to the incision. The retractor comprises a compartment in an elongated or oval shape with a thickened portion on one side that, in a flexible condition, is placed against the tissue at the incision with the thickened portion away from the tissue of the incision. The compartment is then made rigid so that it holds the incision in the open position on its own. The compartment contains a matrix of elastically deformable elements such as polystyrene beads and a fluid such as air. To enable the compartment to change from the flexible condition to the rigid condition, the fluid is evacuated from the compartment through a valve, leaving the elastically deformable beads drawn together rigidly by the collapse of the compartment wall onto the beads and then the compartment is sealed.

A feature of the present invention is the compartment with a flexible condition and a rigid condition and a means for changing the compartment from one condition to the other. This feature allows the compartment to be conformed to a variety of incision shapes and to apply a distributed force for maintaining the incision in the open position against a larger amount of tissue than conventional retractors. The advantage of this feature is its adaptability to a variety of surgical needs and the reduction of trauma to the tissue in contact with the retractor, including skin, organs, nerves, and blood vessels.

Another feature of the present invention is the thickened portion of the compartment which reduces the likelihood that a surgical instrument, for example, will puncture the compartment wall. Although the entire compartment wall can be thickened or made of puncture resistant material, it is usually only necessary to thicken the portion toward the top and inside of the compartment, opposite the incision tissue, when the present retractor is in place.

Still another feature of the present invention is the matrix of material inside the compartment. Preferably comprised of elastically compressible elements and a fluid, the combination of materials in the matrix allows the compartment to be flexible for conforming the retractor to the surgical incision or natural body orifice; however, upon removal of the fluid, a vacuum created in the compartment is satisfied by the collapse of the compartment wall onto the elastically compressible elements, preferably polystyrene beads. As the beads deform, they form a rigid, monolithic pack that maintains its shape and resists the closure of the operative site or natural body orifice. The advantage of this feature is that changing from flexible to rigid conditions is reversible and can be done quickly, which is very important in such surgery.

Another feature hereof, in a preferred embodiment, is a light source carried by the thickened portion of the retractor. The light source is preferably a fiber optic bundle designed to illuminate the interior of the incision. the advantage of this feature is that the light emanates from a location closer to the incision's interior so that interrupiton of the light by the surgeon's head, back and arms is eliminated. Moreover, the light source surrounds the incision thereby reducing the effect of shadows cast by the surgeon's hands.

Still another feature of the present invention is a vacuum or suction source also carried by the thickened portion of the retractor. The suction source is preferably below the light source and more or less parallel thereto. This suction source could be connected to the suction system of the surgical suite. An advantage of this feature is the evacuation of odors, fluids and smoke from within the surgical site. When lasers are used during a surgical procedure, smokey vapors are created which are hazardous to the personnel in the operating room. This feature also improves the visibility for the surgeons.

Other features and advatnages of the present invention will become apparent to those skilled in the art of surgical retractors from a careful reading of the following description and the accompanying drawings which illustrate an embodiment of the invention.

BRIEF DESCRIPTION OF THE DRAWINGS

FIG. 4a is a partial cross-sectional view of the present invention in its flexible condition;

FIG. 4b is a partial cross-sectional view of the present invention of FIG. 4a in its rigid condition;

FIG. 5 is a detailed, cross-sectional view of the valve of the present surgical retractor; and FIG. 6 is a detailed perspective view of the light source of the present surgical retractor.

DETAILED DESCRIPTION OF PREFERRED EMBODIMENTS

Figure 1:
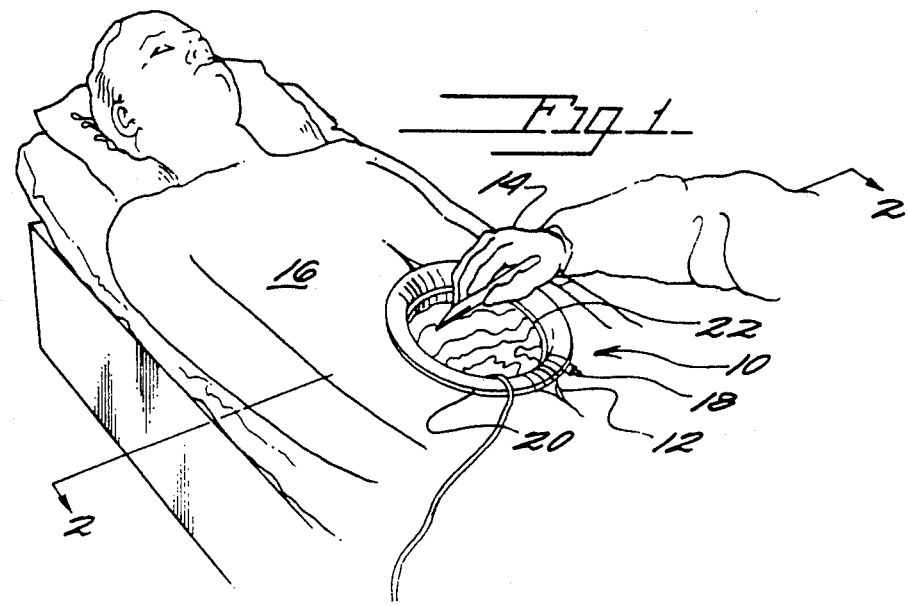
FIG. 1 is a perspective view of a preferred embodiment of the present invention in an abdominal incision.

Referring generally to FIG. 1, there is shown an embodiment of the tractor 10 in place in an abdominal incision 12. This embodiment shows retractor 10 in a generally oval construction maintaining incision 12 in an open configuration. Retractor 10 is shown large enough for a surgeon to put his or her hand 14 into a body 16 to perform the operation. As will be seen, retractor 10 can be made smaller for surgery in confined areas and natural body orifices such vaginal surgery and smaller still for microsurgery.

Retractor 10 has a valve 18 and a thickened portion 20 as shown in FIG. 1. A light source 22, to be further described below, is shown carried by thickened portion 20 to illuminate the interior of incision 12.

Figure 2:
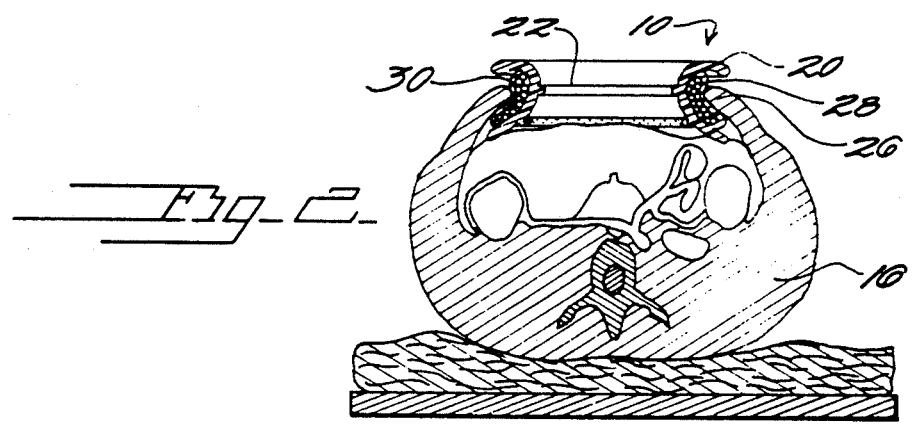
FIG. 2 is a cross-sectional veiw of the present invention taken along line 2—2 of FIG. 1.

In FIG. 2, which shows a cross section of FIG. 1 along line 2—2, retractor 10 is shown to be comprised of a compartment 28 which engages the tissue 26 along the circumference of incision 12 and thickened portion 20 opposite the incision tissue. Compartment 28 contains a matrix 30 of at least one material and can be changed from a flexible condition to a rigid condition. In the rigid condition, retractor is capable of holding incision 12 in the open position. In the flexible condition, retractor 10 may be disengaged from incision 12 or installed against tissue 26 of incision 12.

Figure 3:
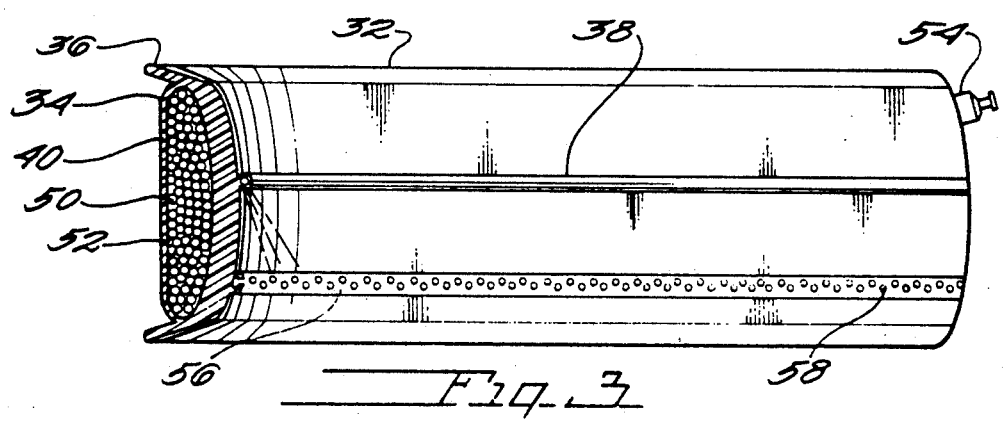
FIG. 3 is a perspective, partially cut away view of an alternative embodiment of the present invention.

Retractor 10 may be made in the form of an oval or in the form of an elongated retractor 32 as shown in FIG. 3. Retractor 32 has a compartment 34 with a thickened portion 36 and a light source 38 carried by thickened portion 36. Thickened portion 36 may be integral with the wall 40 of compartment 34 or may be attached thereto. Thickened portion 36 is to prevent damage to the integrity of wall 40 of compartment 34 from punctures or tears and may be made of puncture resistant or puncture proof material and may be coated or covered with a low friction material such as "TEFLON".

The interior of compartment 34, as with compartment 28, contains a matrix of preferably at least one material. Most preferably, it contains elastically deformable element 50, such as beads, and a fluid 52, such as air or water. A valve 54 is installed in compartment 34 to allow access to the interior so that the fluid 52 can pass into and out of compartment 34. Carried by thickened portion 36 is a suction source 56 which removes odors, fluids, and smokey vapors from the surgery area. Suction source 56 has a plurality of openings 58 to draw into suction source 56 vapors from lasers used in the surgical procedure as well as odors or fluids from the surgical site.

FIGS. 4a and 4b illustrate retractor 10 of FIG. 1 in the flexible condition and the rigid condition, respectively. Retractor 10 is moved into place engaging the tissue of incision 12. In the preferred embodiment, with elastically compressible elements 60 and a fluid 62 forming a matrix in compartment 28, fluid 62 is evacuated from the interior of compartment 28 through valve 18 by a vacuum pump 64. The vacuum created by the loss of fluid 62 causes the wall 66 of compartment 28 to collapse onto elements 60 and pack them into a hard monolith (FIG. 4b) which will hold incision 12 in the open position.

Alternatively, the vacuum may be drawn with the assistance of standard hospital surgery room piped vacuum or with the use of any suitable portable vacuum drawing units available for use in operating rooms as well as a vacuum pump customized for this device.

Alternatively, compartment 28 can be pumped full of fluid until retractor 10 is rigid or matrix 30 (FIG. 2) can be composed of a material that with the addition of a catalyst or water, will cause chemical changes in matrix 30 resulting in a rigid condition.

Valve 18, shown in detail in FIG. 5 has an outer cylinder 70 with a cap 72 and an inner cylinder 74 with a flap 76. Inner cylinder 74 communicates with the interior of compartment 28. Inner and outer cylinders 70 and 74 are joined at one end 78 and proximate at the opposing end 80 so that by removing cap 72 and squeezing outer cylinder 70 with sufficient force to squeeze and deform inner cylinder 74 so that flap 76 no longer seals inner cylinder 74, whereby any vacuum created in compartment 28 is relieved by the in-rushing fluid. However, with cap 72 in place and no pressure on the sides of interior or exterior cylinders 74, 72 respectively, valve 18 holds a vacuum.

FIG. 6 shows a perspective detailed view of a portion of a retractor 90 having a source 92 of illumination carried by a thickened portion 94. Retractor 90 is positioned so that the thickened portion 94 and thus source 92 is interior to an incision so that light from source 92 can illuminate the surgical area. Preferbly, source 92 comprises a bundle 96 of optical fibers 98 in a tube 100 which are individually directed at intervals along tube 100 to the surgical area.

It will be obvious to those skilled in thea rt that many modifications, additions, and substitutions might be made to the present invention without departing from the spirit and scope of the invention which is defined by the appended claims.

What is claimed is:

1. A device for use in holding open a surgical incision, said device comprising:

a compartment having a wall defining an interior surface and an exterior surface, a tissue engaging side of said exterior surface and a tissue opposing side of said exterior surface, said compartment being generally conformable to the shape of said incision, said wall on said tissue opposing side carrying means for resisting punctures;

means for illuminating said incision, said illuminating means carried by said compartment;

a matrix of elastically deformable elements within said compartment;

means for communicating with said interior surface of said compartment so that any fluid in said compartment can be withdrawn and said compartment sealed, said compartment holding said surgical incision open when said fluid is withdrawn and said communicating means sealed.

2. The device as recited in claim 1, wherein said resisting means further comprises a thicker wall.

3. The device as recited in claim 1, wherein said resisting means is a TEFLON coating.

4. The device as recited in claim 1, further comprising means for drawing vapors proximate to said device.

5. The device as recited in claim 1, wherein said device is generally oval and said tissue engaging side is exterior to said oval and said opposing side is interior to said oval.

6. A method of engaging and maintaining tissue of a surgical incision in an open configuration for surgery, comprising:
deploying a compartment about a substantial portion of said incision, said compartment containing a matrix of elastically deformable elements and a fluid;
evacuating at least a portion of said fluid from said compartment so that said elements pack together to cause said compartment to become rigid; and
sealing said compartment.

7. The method as recited in claim 6, wherein said elastically deformable elements are beads.

8. The method as recited in claim 7, wherein said compartment has a wall with a thickened portion and said deployment step further comprises:
placing said compartment against said incision so that said thickened portion is inward of said incision.

9. The method as recited in claim 8, wherein said thickened portion has means for illuminating the interior of said incision and said method further comprises the step of activating said illuminating means.

10. The method as recited in claim 8, wherein said thickened portion has means for suctioning the interior of said incision and said method further comprises the step of activating said suctioning means.

11. The method as recited in claim 7, wherein said compartment has a wall with a thickened portion and said deployment step further comprises:
placing said compartment against said incision so that said thickened portion is inward of said incision and does not engage said tissue.

12. The method as recited in claim 6, wherein said elastically deformable elements are beads and said compartment has means for minimizing punctures of said compartment.

13. The method as recited in claim 6, wherein said compartment has a wall with a thickened portion and said deployment step further comprises:
placing said compartment against said incision so that said thickened portion is inward of said incision and does not engage said tissue.

* * * * *